US008163478B2

(12) United States Patent
Pleines et al.

(10) Patent No.: US 8,163,478 B2
(45) Date of Patent: Apr. 24, 2012

(54) FERTILITY RESTORATION FOR OGURA CYTOPLASMIC MALE STERILE BRASSICA AND METHOD

(75) Inventors: Stephan Christopher Pleines, Bad Salzuflen (DE); Gunther Rudolf-Karl Stiewe, Bad Salzuflen (DE); Katja Brummermann, Bad Salzuflen (DE); Johannes Jacobus Ludgerus Gielen, Saint-Sauveur (FR)

(73) Assignee: Syngenta Participations AG, Basel (CH)

( * ) Notice: Subject to any disclaimer, the term of this patent is extended or adjusted under 35 U.S.C. 154(b) by 1237 days.

(21) Appl. No.: 10/582,696

(22) PCT Filed: Jan. 28, 2005

(86) PCT No.: PCT/EP2005/000877
§ 371 (c)(1),
(2), (4) Date: Mar. 9, 2007

(87) PCT Pub. No.: WO2005/074671
PCT Pub. Date: Aug. 18, 2005

(65) Prior Publication Data
US 2007/0294792 A1    Dec. 20, 2007

(30) Foreign Application Priority Data

Jan. 30, 2004    (GB) .................................. 0402106.9

(51) Int. Cl.
*C12Q 1/68* (2006.01)
(52) U.S. Cl. ........................................................ 435/6.1
(58) Field of Classification Search .................. None
See application file for complete search history.

(56) References Cited

U.S. PATENT DOCUMENTS

| 2002/0032916 A1 | 3/2002 | Charne et al. ................. 800/278 |
| 2002/0049998 A1 | 4/2002 | Burns et al. ................... 800/306 |

FOREIGN PATENT DOCUMENTS

| WO | WO 92/05281 | 4/1992 |
| WO | WO 97/02737 | 1/1997 |
| WO | WO 98/27806 | 7/1998 |
| WO | WO 98/56948 | 12/1998 |
| WO | WO 03/006622 A3 | 1/2003 |
| WO | WO 2004/018636 A3 | 3/2004 |

OTHER PUBLICATIONS

Tulsieram et al. Use of molecular markers for genotype determination of the Ogura Rf gene in Brassica napus. GenBank Accession No. BD192151 (submitted 2003).*

Lowe et al. A computer program for selection of oligonucleotide primers for polymerase chain reactions. Nucleic Acids Res. (1990) vol. 18, No. 7, pp. 1757-1761.*
Ogura, H., "Studies on the New Male-Sterility in Japanese Radish, with Special Reference to the Utilization of this Sterility towards the Practical Raising of Hybrid Seeds," in: *Memoirs of the Faculty of Agriculture*, Kagoshima University, Kagoshima, Japan, Feb. 1968, vol. VI, No. 2, pp. 39-78.
Pelletier, G. et al., "Molecular, Phenotypic and Genetic Characterization of Mitochondrial Recombinants in Rapeseed," Proc $7^{th}$ Int. Rapeseed Conf., Poznan, Poland, 1987, pp. 113-119.
Pellan-Delourme et al., "Cytoplasmic male sterility in rapeseed (*Brassica napus* L.): female fertility of restored rapeseed with "Ogura" and cybrids cytoplasms," Genome, vol. 30, 1988. pp. 234-238.
Makaroff et al., "The *atp6* Coding Region Has Been Disrupted and a Novel Reading Frame Generated in the Mitochondrial Genome of Cytoplasmic Male-sterile Radish," *The Journal of Biological Chemistry*, vol. 264, No. 20, 1989, pp. 11706-11713.
R. Delourme et al., "Radish Cytoplasmic Male Sterility in Rapeseed: Breeding Restorer Lines with a Good Female Fertility," Proc $7^{th}$ Int. Rapeseed Conf., Saskatoon, Canada, 1991, pp. 1506-1510.
R. Delourme et al., "Identification of RAPD markers linked to a fertility restorer gene for the *Ogura* radish cytoplasmic male sterility of rapeseed (*Brassica napus* L.)," *Theor Appl Genet*, vol. 88, 1994, pp. 741-748.
H.S. Janeja et al., "Identification of AFLP markers linked to fertility restorer genes for tournefortii cytoplasmic male-sterility system in *Brassica napus*," *Theor Appl Genet*, vol. 107, 2003, pp. 148-154.

* cited by examiner

*Primary Examiner* — Kenneth R. Horlick
*Assistant Examiner* — David Thomas
(74) *Attorney, Agent, or Firm* — S. Matthew Edwards

(57) ABSTRACT

A *Brassica* plant comprising a unique recombination event resulting from a break at a position along a nucleic acid segment derived from ogura *Raphanus sativus* between the restorer locus and the glucosinolate locus and subsequent rejoining to produce a new recombination event, BLR1. The BLR1 recombination event expresses fertility restoring resulting from expression of the restorer gene derived from *Raphanus sativus* and a GSL content no higher than normal double low open pollinated varieties. The *Brassica* inbred line BLR-038, Deposit Number NCIMB-41193, is one example of a plant that contains the BLR1 recombination event. The BLR1 recombination event is introgressed into different *Brassica* genetic backgrounds using breeding techniques known to those skilled in the art. For example, the *Brassica* inbred line BLR-038 or another *Brassica* plant containing the BLR1 recombination event may be crossed with male sterile inbreds to produce hybrids expressing low GSL content and superior agronomic traits.

12 Claims, No Drawings

FERTILITY RESTORATION FOR OGURA CYTOPLASMIC MALE STERILE *BRASSICA* AND METHOD

This invention relates to a novel fertility restorer locus for Ogura cytoplasmic male sterile *Brassica* plants.

Oilseed rape (*Brassica napus*), also referred to as canola (annual spring type) or winter oilseed rape (biannual type), is derived from interspecific hybridization of *B. oleracea* and *B. campestris*. Breeding between *Brassica* species is common. Generally, winter-type rapeseed is grown in North Western Europe, whereas spring-types are grown in Canada, China, India, Australia and South America mainly.

Oilseed rape is becoming an increasingly important crop, valued for edible and industrial oil usage and for its seed meal rich in protein. Wide acceptance of rapeseed meal for animal nutrition is hampered by the presence in the seed of sulfur compounds called glucosinolates (GSLs). Glucosinolates are undesirable in *Brassica* seeds since they can lead to the production of antinutritional breakdown products upon enzymatic cleavage during oil extraction and digestion. Although the development of superior, edible oil had been achieved in the early 1970s through introduction of rapeseed varieties with less than 2% of erucic acid in percent of their total fatty acid profile (single zero quality), the continuing presence of glucosinolates in the high protein meal remained a major constraint to further market expansion.

At present the maximum threshold for GSL free rapeseed varieties set by European law is 25 µmol total glucosinolate (GSL) per gram (g) of seed at 9% humidity (EU decree 2294/92). Doublelow spring canola varieties cultivated in Canada need to have GSL levels of less than 30 µmoles of glucosinolates per gram of air-dried oil-free meal. The GSL levels of commonly cultivated double zero oilseed rape varieties in Europe and Canada varies significantly below the threshold levels at 60% of the official threshold level or even lower. At present, hybrid *Brassica* plants based on the Ogura hybrid system having seeds with low GSL content express inferior agronomical traits such as lower seed yields, poor disease resistances and lodging susceptibility.

Hybrid cultivars are desired because of potentially higher seed yield due to heterosis. To produce hybrid *Brassica* plants breeders use self-incompatible (SI), cytoplasmic male sterile (CMS), or nuclear male sterile (NMS) *Brassica* plants as the female parent. SI plants are not able to self pollinate due to their genetic constitution and CMS and NMS female plants are incapable of producing pollen. Thus, all these plants must be cross-pollinated by a male parent. A number of CMS systems are used for hybrid seed production of *Brassica*: Polima (pol), nap, tournefortii, Koscna, and Ogura (ogu). (See for example Ogura (1968) Mem. Fac. Agric. Kagoshima Univ. 6:39-78; Makaroff (1989 Journal of Biol. Chem. 264: 11706-11713; U.S. Pat. No. 5,254,802.) The ogu system, thought to be the most useful, is based on the use of a male sterility determinant derived from *Raphanus sativus* cytoplasm. F1 seed produced from a cross between an Ogura CMS female *Brassica* plant and a normal male *Brassica* plant will be male sterile. In other words, plants grown from the F1 seed will not produce pollen. To produce a male fertile F1 generation plant, a restorer gene must be present in the male parent of the F1 hybrid.

A fertility restorer locus was transferred from Raphanus sativus to *Brassica* CMS plants by Institut National de la Recherche Agronomique (INRA) in Rennes, France (Pelletier et al., 1987) Proc 7$^{th}$. Int. Rapeseed Conf., Poznan, Poland: 113-119). The restorer gene (Rf) originating from *Raphanus sativus* is described in WO92/05251 and in Delourme et al. ((1991) Proc. 8$^{th}$. Int. Rapeseed Conf. Saskatoon, Canada: 1506-1510). The original restorer inbreds and hybrids carrying this Rf gene express elevated glucosinolate levels and a decrease in seed set (Pellan-Delourme and Renard, 1988 Genome 30: 234-238, Delourme et al., 1994 Theor. Appl. Genet. 88: 741-748). In seed grown on Ogu Rf hybrid plants, the glucosinolate levels are elevated even when the female parent has reduced glucosinolate content. Recombination at the radish chromosomal region surrounding the Rf gene is suppressed in Brassica and therefore different recombination events in this region are difficult to obtain. The link between the Rf gene and the glucosinolate locus has been broken (WO98/27806). However, it is difficult to break the linkage between the glucosinolate gene and the restorer gene and still maintain line stability and superior combining ability for the production of high value commercial hybrid seed. Therefore, there is a need to develop a recombination event that unlinks the restorer gene from the glucosinolate gene while maintaining a *Brassica* plant's ability to produce high value commercial hybrid seed.

The current invention provides a *Brassica* plant that comprises a recombination event resulting from a break between the fertility restorer locus for Ogura cytoplasmic male sterility derived from the Ogura *Raphanus sativus* and the glucosinolate locus along a nucleic acid segment and subsequent rejoining to produce a new nucleic acid segment, referred to herein as the BLR1 recombination event.

In one embodiment, the invention relates to a *Brassica* plant comprising a DNA fragment including a fertility restorer locus for Ogura cytoplasmic male sterility, wherein said DNA fragment can be identified through at least one marker of bin 2, but cannot be detected by at least one marker of bin 3.

In one embodiment, the invention relates to a *Brassica* plant comprising a DNA fragment including a fertility restorer locus for Ogura cytoplasmic male sterility, wherein said DNA fragment can be identified through at least one marker of bin 2, but none of the markers of bin 3.

In one embodiment, the invention relates to a *Brassica* plant comprising a DNA fragment including a fertility restorer locus for Ogura cytoplasmic male sterility, wherein said DNA fragment can be identified through all the markers of bin 2, but none of the markers of bin 3.

In another embodiment, the invention relates to a *Brassica* plant comprising a DNA fragment including a fertility restorer locus for Ogura cytoplasmic male sterility according to the invention, wherein bin 2 is comprised of the markers selected from the group consisting of E33M47, E2M4-1, E3M1-1, E4M14-1, E5M1-2, E5M4-2, and E8M14-2, and bin 3 is comprised of the markers selected from the group consisting of OPY17, OPN20, and E8M1-2.

In still another embodiment, the invention relates to a *Brassica* plant according to the invention, wherein the above mentioned markers are amplified in a polymerase chain reaction using primer pairs represented by 1159 and 1160; E2 and M4; E3 and M1; E4 and M14; E5 and M1; E5 and M4; E8 and M14, respectively. The above primers are essentially characterized by the nucleotide sequence given in SEQ ID NO: 13 (1159), SEQ ID NO: 14 (1160), SEQ ID NO: 25 (E2), SEQ ID NO: 26 (M4), SEQ ID NO: 29 (E3), SEQ ID NO: 30 (M1), SEQ ID NO: 32 (E4), SEQ ID NO: 28 (M14), SEQ ID NO: 33 (E5), and SEQ ID NO: 37 (E8), respectively.

In a specific embodiment, the invention relates to a *Brassica* plant according to the invention, wherein said markers are amplified in a polymerase chain reaction using the primer pairs represented by PR0004F and PR0004R; 1135 and 1136; and E8 and M1, respectively. The above primers are essentially characterized by the nucleotide sequence given in SEQ ID NO: 19 (PR0004F), SEQ ID NO: 20 (PR0004R), SEQ ID NO: 3 (1135), SEQ ID NO: 4 (1136), SEQ ID NO: 37 (E8), and SEQ ID NO: 30 (M1), respectively.

In another embodiment, the invention relates to a *Brassica* plant according to the invention comprising a DNA fragment including a restorer gene, wherein said DNA fragment is the BLR1 recombination event.

In a specific embodiment, the *Brassica* plant according to the invention is an inbred plant.

In a further specific embodiment, the *Brassica* plant according to the invention is a hybrid plant.

In another embodiment, the invention relates to a *Brassica* plant according to the invention comprising a DNA fragment including a fertility restorer locus for Ogura cytoplasmic male sterility, wherein said DNA fragment is the BLR1 recombination event and said BLR1 recombination event is obtainable from the *Brassica* inbred line BLR-038, a sample of the seed of inbred line BLR-038 having been deposited with NCIMB under accession number NCIMB 41193.

In a further embodiment, the invention relates to a method of detecting a *Brassica* plant containing a fertility restorer locus for Ogura cytoplasmic male sterility, comprising the steps of:
  a) obtaining a sample from a *Brassica* plant;
  b) detecting in said sample a DNA fragment that can be identified using a marker of bin 2, but not by a marker of bin 3.

In one embodiment, the invention relates to a method of detecting a *Brassica* plant containing a restorer gene, comprising the steps of:
  a) obtaining a sample from a *Brassica* plant;
  b) detecting in said sample a DNA fragment by using
    i) at least one marker of bin 2, but not by at least one marker of bin 3;
    ii) at least one marker of bin 2, but none of the markers of bin 3;
    iii) all the markers of bin 2, but none of the markers of bin 3

In another embodiment, the method of detecting a *Brassica* plant according to the invention, further comprises the step of c) selecting said *Brassica* plant, or a part thereof, containing said DNA fragment.

In still another embodiment, the method of detecting a *Brassica* plant according to the invention, further comprises the step of d) selfing said *Brassica* plant containing said DNA fragment.

In still another embodiment, the method of detecting a *Brassica* plant according to the invention, further comprises the step of e) crossing said *Brassica* plant with another Brassica plant.

In one embodiment, the invention relates to a method of detecting a *Brassica* plant according to the invention, wherein said DNA fragment comprises the BLR1 recombination event.

In another embodiment, the invention relates to a method of detecting a *Brassica* plant according to the invention, wherein in step b) said marker of bin 2 comprises a marker selected from the group consisting of E33M47, E2M4-1, E3M1-1, E4M14-1, E5M1-2, E5M4-2, and E8M14-2.

In a specific embodiment, the invention relates to a method of detecting a *Brassica* plant according to the invention, wherein in step b) said marker of bin 2 has partial homology to a marker selected from the group consisting of E33M47, E2M4-1, E3M1-1, E4M14-1, E5M1-2, E5M4-2, and E8M14-2.

In another embodiment, the invention relates to a method of detecting a *Brassica* plant according to the invention, further comprising the step of f) detecting in said sample a DNA fragment obtainable by PCR amplification using primers 1159 and 1160, whereas said DNA fragment is not amplified by the primers PR0004F and PR0004R, and wherein said markers are essentially characterized by a nucleotide sequence given in SEQ ID NO: 13 (1159), SEQ ID NO: 14 (1160) and SEQ ID NO: 19 (PR0004F), SEQ ID NO: 20 (PR0004R), respectively.

In one embodiment, the invention relates to a combination of markers for detecting the presence of the BLR1 recombination event, comprising at least one marker of bin 2 and at least one marker of bin 3.

In another embodiment, the invention relates to a combination of markers for detecting the presence of the BLR1 recombination event according to the invention, wherein said combination of markers comprises at least one marker of bin 2 selected from the group consisting of E33M47, E2M4-1, E3M1-1, E4M14-1, E5M1-2, E5M4-2, and E8M14-2 and at least one a marker of bin 3 selected from the group consisting of OPY17, OPN20, and E8M1, or a combination of markers comprising one or more markers having partial homology to any one of these markers.

In one embodiment, the invention relates to a method for screening a *Brassica* plant to determine whether it contains the BLR1 recombination event, comprising extracting DNA from said *Brassica* plant, subjecting the extraction to a polymerase chain amplification reaction in the presence of DNA fragments represented by primers 1159, 1160, PR0004F, and PR0004R, and determining the amplification of DNA fragments from the extracted DNA by primers 1159 and 1160 and lack of amplification of DNA fragments from extracted DNA that correspond to primers PR0004F and PR0004R.

In one embodiment, the invention relates to a method for producing a fertile F1 hybrid *Brassica* plant comprising the steps of crossing a *Brassica* male fertile plant comprising the BLR1 recombination event with a *Brassica* CMS male sterile plant to produce F1 hybrid seed.

In another embodiment, the invention relates to a method for producing a fertile F1 hybrid *Brassica* plant comprising the steps of
  a) determining total glucosinolate content in the male fertile restorer parent comprising the BLR1 recombination event and, optionally, also in the female male sterile CMS parent;
  b) crossing the female and male parents to produce F1 hybrid seed.

In still another embodiment, the invention relates to a method for producing a fertile F1 hybrid *Brassica* plant comprising the steps of
  a) detecting in seed or a plant of the male fertile restorer parent the BLR1 recombination event through marker analysis;
  b) crossing the female and male parents to produce F1 hybrid seed.

In a specific embodiment of the invention, the presence of the male restorer gene in seed or a plant of the restorer parent are detected by determining total glucosinolate content in the male fertile restorer parent and through marker analysis.

In another embodiment, the method for producing a fertile F1 hybrid *Brassica* plant according to the invention comprises the additional step of planting said F1 hybrid seed.

In another embodiment, the method for producing a fertile F1 hybrid *Brassica* plant according to the invention comprises the additional step of harvesting the F2 seed grown from the plant resulting from said F1 seed.

In another embodiment, the method for producing a fertile F1 hybrid *Brassica* plant according to the invention comprises the additional step of determining total glucosinolate content in F2 seed derived from the F1 hybrid plant.

In one embodiment, the invention relates to a hybrid F1 *Brassica* plant produced by the method according to the invention.

In a further embodiment, the invention relates to a *Brassica* plant comprising the BLR1 recombination event, wherein said event is obtainable from the *Brassica* inbred line BLR-038, a sample of the seed of inbred line BLR-038 having been deposited with NCIMB under accession number NCIMB 41193.

In a further embodiment, the invention relates to a method for producing a *Brassica* plant containing the BLR1 recombination event comprising the steps of obtaining a *Brassica* plant containing the BLR1 recombination event, crossing this plant with a another *Brassica* plant, obtaining hybrid seed produced by this cross, and planting said hybrid seed to produce a *Brassica* plant containing the BLR1 recombination event.

In one embodiment, the invention relates to a kit for detecting the BLR1 recombination event comprising:
 a) a first pair of primers that amplify a marker of bin 2; and
 b) a second pair of primers that do not amplify a marker of bin 3.

In one embodiment, the invention relates to a *Brassica* plant comprising the BLR1 recombination event.

In a further embodiment, the invention relates to a *Brassica* plant according to the invention, wherein the BLR1 recombination event is obtainable from the *Brassica* inbred line BLR-038.

In another embodiment, the invention relates to a *Brassica* plant according to the invention, wherein said plant is a *Brassica napus, Brassica campestris, Brassica oleracea, Brassica nigra, Brassica carinata* or any other specie belonging to the Brassicacea family.

In still another embodiment, the invention relates to a *Brassica* plant according to the invention, wherein said plant is a sexual or asexual recombination or clone of said species.

In a further embodiment, the invention relates to a *Brassica* plant according to the invention, said plant comprising a total glucosinolate level equal to or lower than the glucosinolate levels of double-low *Brassica* varieties.

The current invention provides a *Brassica* plant comprising a unique recombination event, referred to herein as the BLR1 recombination event, due to a break at a position along the nucleic acid segment between the restorer locus and the glucosinolate locus. *Brassica* plants of the present invention express fertility restoring resulting from expression of the *Raphanus sativus* restorer gene and a GSL content no higher than that normally found in double low open pollinated varieties. The *Brassica* inbred line BLR-038, Deposit Number NCIMB-41193, is one example of a plant that contains the BLR1 recombination event. Using breeding techniques known to those skilled in the art and as briefly described herein, inbred line BLR-038 and other inbred lines containing the BLR1 recombination event are crossed with male sterile inbreds to produce hybrids expressing low GSL content and superior agronomic traits. More generally, the present invention further includes transferring the BLR1 recombination event of the present invention from one *Brassica* plant to another *Brassica* plant of the same or a different subspecies. A further aspect of the invention is a kit and method including markers and the use of markers of specified bins to select *Brassica* plants that contain the BLR1 recombination event.

Plants of the present invention containing a recombination event resulting from a break between the restorer locus derived from the Ogura *Raphanus sativus* and the glucosinolate locus along a nucleic acid segment and subsequent rejoining to produce a new nucleic acid segment, exemplified herein by the BLR1 recombination event and expressing fertility restoring resulting from expression of the *Raphanus sativus* restorer gene and a GSL content no higher than that normally found in doublelow open pollinated varieties, can be obtained by applying a breeding scheme as outlined below (see Table 1 for details of the breeding history of BLR1, a recombination event, which is a recombination of the Ogura *Raphanus sativus* restorer locus). A CMS inbred line such as, for example, line R30195 can be crossed with a male inbred line containing a restorer gene such as, for example inbred line R40 (Delournme et al, 1999; http://www.regional.org.au/au/gcirc/4/383.htm), which contains the restorer gene from *Raphanus sativus* transferred to *Brassica* CMS plants by Institut National de la Recherche Agronomique (INRA) in Rennes, France (Pelletier et al., 1987) Proc $7^{th}$. Int. Rapeseed Conf., Poznan, Poland: 113-119), to produce F1 hybrids. R40 is a generation F6 offspring produced via selfings from the original cross (Fu 58.Darmor B1F1×Rest. Darmor B1F1)× Bienvenu. F1 hybrids resulting from the cross of a CMS inbred line with a male inbred line comprising a restorer gene (e.g. cross R30195×R40 containing the CMS-restorer gene) are selected based on male fertility, which is determined at flowering. The F1 hybrid plants (e.g. F1 hybrid 92HR013) are crossed with a non-CMS, non-restorer double zero quality breeding line such as, for example, breeding line 93B-1-3. Seeds of fertile plants resulting from such a cross with a non-CMS, non-restorer double zero quality breeding line (e.g. 93B-1-3) are grown and the resulting CMS restorer plants may again be crossed with the same or an alternative double low quality breeding line such as, for example, breeding line 92/19047. The lines resulting from this cross are selfed several times (selfings made from 1995 through 2002 are shown in Table 1).

In all plots, segregation of male fertility can be observed, meaning that all plots contained heterozygous and homozygous maintainer and restorer plants. Because all crosses are initially made in the Ogura CMS cytoplasm and this cytoplasm is maintained in all future generations the maintainer genotypes turn out to be male sterile. Plants may be selfed using plastic bags to cover the inflorescence before flowering. The bag is preferably maintained over the plant during the whole flowering period to avoid cross-pollination.

The glucosinolate (GSL) content of the *Brassica* seeds is monitored throughout the breeding program. Glucosinolate content is given in µmol/g of seed at 9% humidity. The glucosinolate analysis can be performed using state in the art technology such as, for example, HPLC or near-infrared reflectance spectroscopy (NIRS). Using the NIRS method, it is possible to analyze samples of undestroyed *Brassica* seed on their quality components oil, protein and glucosinolate.

*Brassica* plants according to the present invention comprising a unique recombination event due to a break at a position along the nucleic acid segment between the restorer locus and the glucosinolate locus such as, for example, a recombination event referred to herein as the BLR1 recombination event, have a glucosinolate (GSL) content in the seed derived from said plant which is equal to or lower than the glucosinolate levels normally found in doublelow open pollinated varieties, preferably below 18 µmol total glucosinolate (GSL) per gram (g) of seed at 9% humidity and up to a level coming close to 0 µmol total glucosinolate (GSL) per gram (g) of seed at 9% humidity.

In a specific embodiment of the invention, the GSL content is in a range of between 0.5 to 18 μmol total glucosinolate (GSL) per gram (g) of seed at 9% humidity, particularly in a range of between 2 and 15 μmol total glucosinolate (GSL) per gram (g) of seed at 9% humidity, more particularly in a range of between 3 and 14 μmol total glucosinolate (GSL) per gram (g) of seed at 9% humidity, but especially a GSL content of between 3.5 and 10 μmol total glucosinolate (GSL) per gram (g) of seed at 9% humidity. In a specific embodiment of the invention, the GSL content is in a range of between 3.6 and 6.0 μmol, but especially between 3.6 and 4.2 μmol total glucosinolate (GSL) per gram (g) of seed at 9% humidity.

A *Brassica* plant of the present invention expresses fertility restoring resulting from expression of the *Raphanus sativus* restorer gene and a GSL content no higher than normal doublelow open pollinated varieties (varieties low in erucic acid in the oil and low in GSL in the solid meal remaining after oil extraction). The *Brassica* inbred line BLR-038, Deposit Number NCIMB-41193, is one example of a plant that contains the BLR1 recombination event of the invention. Using breeding techniques known to those skilled in the art and as briefly described herein, the BLR1 recombination event can be introgressed into any Brassica plant capable of being crossed with inbred line BLR-038. Inbred line BLR-038 and other plants containing the BLR1 recombination event of the invention are crossed with male sterile inbreds, especially inbreds expressing low GSL content and/or favorable agronomic properties such as high resistance to plant pathogens, good standability, high oil content, high yield, etc, to produce hybrids with low GSL content and superior agronomic traits. More generally, the present invention also includes transferring the BLR1 recombination event of the present invention from one *Brassica* plant to another. The present invention further includes the use of marker-assisted selection to select *Brassica* plants containing the BLR1 recombination event.

In one embodiment, the invention discloses markers that reveal polymorphism between the plants that carry the Ogura Rf translocation and the homozygous recessive (rfrf) bulk. Such markers allow for the comparison of *Brassica* plants comprising a unique recombination event resulting from a break at a position along a nucleic acid segment between the restorer locus derived from Ogura *Raphanus sativus* and the glucosinolate locus and subsequent rejoining to produce a new recombination event such as, for example, *Brassica* inbred line BLR-038, to published restorer inbred lines such as, for example, Pioneer hybrids (ATCC 209002, 97839, 97838, 209001), and to SERASEM's commercial hybrid Lutin containing the restorer locus released by INRA. The markers are binned according to their amplification profile across the various plant materials resulting in four different classes of markers. Within the meaning of the present application a bin refers to a nucleic acid or chromosome segment flanked by breaking points, wherein said bins can be identified and are represented by a set of markers mapping between the breaking points bracketing the bin and grouped according to their location along a nucleic acid segment. Lines containing bin 4 markers contain the longest fragment. Fragment length is decreasing with decreasing bin number.

Bin 1 comprises AFLP markers selected from the group consisting of E5M16-1, E5M4-3, E6M3-2, and E8M14-1, or a marker having partial homology to any one of these markers.

Bin 2 comprises ALFP markers selected from the group consisting of E2M4-1, E3M1-1, E4M14-1, E5M1-2, E5M4-2, and E8M14-2, or a marker having partial homology to any one of these markers.

Bin 3 comprises the AFLP marker E8M1-2, or a marker having partial homology to any one of these markers.

Bin 4 comprises AFLP markers selected from the group consisting of E2M13-1, E2M14-1, E3M12-1, and E6M3-1, or a marker having partial homology to any one of these markers.

In one embodiment, the invention relates to a *Brassica* plant comprising a *Raphanus sativus* DNA fragment including a restorer gene, wherein said DNA fragment can be identified using at least one marker of bin 2, but not to a marker of bin 3.

In a further embodiment, the invention relates to a *Brassica* plant comprising a *Raphanus sativus* DNA fragment including a restorer gene, wherein said DNA fragment can be identified using all markers of bin 2, but not to a marker of bin 3.

In particular, the invention relates to a *Brassica* plant comprising a *Raphanus sativus* DNA fragment including a fertility restorer locus for Ogura cytoplasmic male sterility, wherein said DNA fragment can be identified through the presence of at least one marker of bin 2, but can not be identified by at least one marker of bin 3, and wherein the DNA fragment is the BLR1 recombination event of the present invention.

The "at least one marker of bin 2" may be one, two, three, four, five, six or all the markers selected from the group consisting of E33M47, E2M4-1, E3M1-1, E4M14-1, E5M1-2, E5M4-2, and E8M14-2 including all possible permutations of different numbers of markers within this group.

The "at least one marker of bin 3" may be one, two or all the markers selected from the group consisting of OPY17, OPN20, and E8M1-2 including all possible permutations of different numbers of markers within this group.

Also comprised within the scope of the invention are all possible combinations of at least one marker of the bin 2 group of markers and at least one marker of the bin 3 group of markers.

In a further embodiment, the present invention relates to a marker of bin 2 selected from the group consisting of E33M47, E2M4-1, E3M1-1, E4M14-1, E5M1-2, E5M4-2, and E8M14-2, and/or a marker of bin 3 selected from the group consisting of OPY17, OPN20, and E8M1-2 including all possible combination of one or more markers within each group (bin) and/or between the two groups (bins)

In particular, the present invention relates to a marker selected from the group consisting of E33M47, E2M4-1, E3M1-1, E4M14-1, E5M1-2, E5M4-2 and E8M14-2, which is amplified in a polymerase chain reaction using primer pairs represented by 1159 (SEQ ID NO: 13) and 1160 (SEQ ID NO: 14); E2 (SEQ ID NO: 25) and M4 (SEQ ID NO: 26); E3 (SEQ ID NO: 29) and M1 (SEQ ID NO: 30); E4 (SEQ ID NO: 32) and M14 (SEQ ID NO: 28); E5 (SEQ ID NO: 33) and M1 (SEQ ID NO: 30); E5 (SEQ ID NO: 33) and M4 (SEQ ID NO: 26), and E8 (SEQ ID NO: 37) and M14 (SEQ ID NO: 28), respectively. The above-mentioned primers are also part of the invention as well as the specific primer combinations provided herein.

The present invention also includes a marker selected from the group consisting of OPY17, OPN20, and E8M1-2, which is amplified in a polymerase chain reaction using the primer pairs represented by PR0004F (SEQ ID NO: 19) and PR0004R (SEQ ID NO: 20); 1135 (SEQ ID NO: 3) and 1136 (SEQ ID NO: 4); and E8 (SEQ ID NO: 37) and M1 (SEQ ID NO: 30). The above-mentioned primers are also part of the invention as well as the specific primer combinations provided herein.

In a further embodiment, the present invention relates to a method of detecting a *Brassica* plant containing a restorer gene derived from *Raphanus sativus*, comprising the steps of: obtaining a plant sample from a *Brassica* plant, detecting in the sample a DNA fragment that can be identified using at least one marker of bin 2, but can not be detected by at least one marker of bin 3.

In a further embodiment, the present invention relates to a method of detecting a *Brassica* plant containing a restorer gene derived from *Raphanus sativus*, comprising the steps of: obtaining a plant sample from a *Brassica* plant, detecting in the sample a DNA fragment that can be detected by a marker of bin 2, but not by a marker of bin 3. The method further includes selecting the *Brassica* plant, or a part thereof, containing the DNA fragment, and also selfing the *Brassica* plant containing the DNA fragment. In a specific embodiment of the invention, the DNA fragment comprises the BLR1 recombination event.

In particular, the present invention relates to a method of detecting a *Brassica* plant containing a DNA fragment comprising a restorer gene derived from *Raphanus sativus*, particularly a DNA fragment comprising the BLR1 recombination event, wherein the marker of bin 2 comprises at least one marker selected from the group consisting of E33M47, E2M4-1, E3M1-1, E4M14-1, E5M1-2, E5M4-2, and E8M14-2.

The invention includes a method of detecting a *Brassica* plant, wherein the marker of bin 2 has partial homology to a marker selected from the group consisting of E33M47, E2M4-1, E3M1-1, E4M14-1, E5M1-2, E5M4-2, and E8M14-2.

The method of the invention includes the step of detecting in a plant sample a DNA fragment obtainable by PCR amplification using primers 1159 (SEQ ID NO: 13) and 1160, (SEQ ID NO: 14) whereas the DNA fragment is not amplified by the primers PR0004F (SEQ ID NO: 19) and PR0004R (SEQ ID NO: 20), respectively.

The present invention also includes a combination of markers for detecting the presence of the BLR1 recombination event, comprising at least one marker of bin 2 and at least one marker of bin 3.

The present invention further includes a combination of one or more markers of bin 2 selected from the group consisting of E33M47, E2M4-1, E3M1-1, E4M14-1, E5M1-2, E5M4-2, and E8M14-2 and one or more markers of bin 3 selected from the group consisting of OPY17, OPN20, and E8M1, or a marker having partial homology to any one of these markers.

Also provided herein are markers, which enable the breeder to determine the genotype of a *Brassica* plant comprising the Ogura Rf gene. The breeder can then distinguish between homozygous and heterozygous Ogura restorer lines in individual plants of segregating populations by using a combination of two marker pairs, especially two SCAR marker pairs, one of which is linked to the restorer gene ("Rf") and one to the absence of the restorer gene ("rf") as described, for example, in CA 2,206,673.

The markers can be identified by carrying out two PCR reaction, one involving a primer pair capable of hybridizing with the "Rf" marker such as, for example, primer pair 1137 (SEQ ID NO: 5) and 1138 (SEQ ID NO: 6) and one involving markers capable of hybridizing with the "rf" marker such as, for example, primer pair PR0001F1 (SEQ ID NO: 40) and PR0001R1 (SEQ ID NO: 41). In plants homozygous for the "Rf" gene, the PCR reaction will only identify the marker that is linked to the "Rf" gene. In plants homozygous for the "rf" gene, the PCR reaction will only identify the marker that is linked to the "rf" gene. In a heterozygous plant with both the "Rf" and the "rf" gene present, the PCR reaction will give bands, which are representative for both the "Rf" and the "rf" marker.

The PCR reaction may be a single PCR reaction, wherein each DNA sample is treated separately or a multiplex PCR reaction, wherein the two sets of primer pairs are used together in one single PCR reaction.

The present invention also includes a method for screening a population of *Brassica* plants to determine whether it contains a plant comprising the BLR1 recombination event, comprising extracting DNA from the *Brassica* plant, subjecting the *Brassica* plant extraction to a polymerase chain amplification reaction in the presence of primers 1159, 1160, PR0004F, PR0004R, and determining the amplification of DNA fragments from the extracted DNA by primers 1159 and 1160 and lack of amplification of DNA fragments from extracted DNA by primers PR0004F and PR0004R, thereby indicating the presence of the BLR1 recombination event.

The present invention includes a kit and method that incorporate one or more of markers falling within bin 2 and one or more markers falling within bin 3 to detect the presence of the BLR1 recombination event in a plant or a plant part. According to the invention, plant material that contains the BLR1 recombination event can be identified using at least one marker of bin 2, but not to at least one marker of bin 3.

The present invention further includes a method of introgressing the BLR1 recombination event comprising the steps of obtaining a *Brassica* plant containing the BLR1 recombination event such as, for example, the *Brassica* inbred line BLR-038, Deposit Number NCIMB 41193 deposited on Aug. 28, 2003, crossing this plant with another *Brassica* plant, producing hybrid seed and selecting hybrid seed containing the BLR1 recombination event.

In particular, a *Brassica* plant containing the BLR1 recombination event such as, for example, the *Brassica* inbred line BLR-038, Deposit Number NCIMB 41193 deposited on Aug. 28, 2003 is crossed with a high performing winter oilseed rape breeding line, which is used as recurrent parent. In these crosses, the *Brassica* inbred line is used as female to maintain the CMS cytoplasm.

The resulting F1 plants are crossed with the recurrent parent to replace more of the genome of the *Brassica* inbred line, particularly between 80 to 99.5% of the genome, more particularly between 90% and 99% of the genome, but especially between 95% and 98% of the genome. In every generation, the presence or absence of the restorer genes must be determined. Due to the CMS cytoplasm in every generation the presence or absence of the restorer gene can be easily detected, for example, by fertility scoring.

After the last backcross generation a selfing step is required. In the following generation molecular markers are used as described in this invention to select plants homozygous for the restorer gene. These plants represent the restorer line, which can be used to produce hybrid seed.

A different way to obtain a restorer line is for example to cross a breeding line containing the BLR1 recombination event such as, for example, the *Brassica* inbred line BLR-038. The fertile F1 plants are selfed. In the F2 generation homozygous restorer plants are detected in the greenhouse by using a marker analysis such as that described herein before and the homozygous plants are selfed.

F3 descendants of the homozygous F2 plants are planted into the field to select only within the desired homozygous restorer plants. F3 plants are then selfed. The selfing procedure is repeated until the line has the sufficient homogeneity for the use as a hybrid component.

Test crosses are performed by using several CMS Ogura male sterile lines as the female parents with a set of genetically different F3 or subsequent generation inbred plants containing the BLR1 recombination event of the invention as male parents. The descendants are sown in the greenhouse and fertile and sterile plants are counted during flowering. Plants containing BLR1 recombination event can also be selected using the kit and method described herein.

In a further embodiment, the present invention also relates to a *Brassica* plant comprising the BLR1 recombination event, wherein said event is obtainable from the *Brassica* inbred line BLR-038, a sample of the seed of inbred line BLR-038 having been deposited with NCIMB under accession number NCIMB 41193.

In one embodiment, the present invention relates to a method for producing a fertile F1 hybrid *Brassica* plant comprising the steps of crossing a *Brassica* male fertile plant comprising the BLR1 recombination event with a *Brassica* CMS male sterile plant to produce F1 fertile seed, further comprising the step of planting said F1 hybrid seed, and further comprising the step of harvesting the F2 seed grown from the plant resulting from said F1 seed, and includes F1 hybrid *Brassica* plants developed by this method.

Since the male-sterile, female CMS A-line cannot self-pollinate, it must be maintained by crossing said A-line with a maintainer B-line that is male fertile and genetically identical to the A-Line. The result of this cross is a male-sterile CMS A-line. The restorer R-line can be maintained by selfing.

The restorer R-line is crossed with the male sterile CMS A-line to produce F1 seed produced on the A-line. The F1 seed may be sold commercially for the production of F2 seed. The F2 seed of the invention has a low glucosinolate level, particularly a GSL Level below 18 μmol total glucosinolate (GSL) per gram (g) of seed at 9% humidity and up to a level coming close to 0 μmol total glucosinolate (GSL) per gram (g) of seed at 9% humidity.

Deposit

A seed sample of *Brassica* inbred line BLR-038 was deposited with NCIMB, Ltd, 23 St Machar Drive, Aberdeen AB24 3RY, Scotland, UK, on Aug. 28, 2003, Deposit Number NCIMB 41193.

EXAMPLES

The following examples are intended to provide illustrations of the application of the present invention. The following examples are not intended to completely define or otherwise limit the scope of the invention.

Example 1

Breeding History of the *Brassica* Inbred Line BLR038 and GSL Characterization

Table 1 describes the breeding history of plants of the present invention containing the BLR1 recombination event, which is a recombination of the Ogura Raphanus sativus restorer locus. In year 1992, the CMS inbred line R30195 was crossed with the male inbred line R40 containing the restorer gene of INRA, to produce F1 hybrids. R40 is a generation F6 offspring produced via selfings from the original cross (Fu 58.Darmor B1F1×Rest. Darmor B1F1)×Bienvenu. F1 hybrids from the cross R30195×R40 with the CMS-restorer gene were selected based on male fertility, which was determined at flowering. The F1 hybrid plants (92HR013) were crossed with a non-CMS, non-restorer double zero quality breeding line 93B-1-3. In 1994, seeds of fertile plants resulting from the cross with 93B-1-3 were grown and the resulting CMS restorer plants were crossed with the double low quality breeding line 92/19047. The lines resulting from this cross were selfed several times from 1995 through 2002 as shown in Table 1. In all plots, segregation of male fertility was observed, meaning that all plots contained heterozygous and homozygous maintainer and restorer plants. Because all crosses were initially made in the Ogura CMS cytoplasm and this cytoplasm was maintained in all future generations the maintainer genotypes turned out to be male sterile. Plants were selfed using plastic bags to cover the inflorescence before flowering. The bag was maintained over the plant during the whole flowering period to avoid cross-pollination.

The GSL content of the *Brassica* seeds was monitored throughout the development of inbred line BLR-038. Glucosinolate content is given in μmol/g of seed at 9% humidity. The glucosinolate analysis was performed using the near-infrared reflectance spectroscopy. Using this method, it is possible to analyze samples of undestroyed *Brassica* seed on their quality components oil, protein and glucosinolate. The analyses were performed on a FOSS NIR Systems Model 5000-c. Glucosinolate analysis is described in P. Williams and D. Sobering, (1992) In: Hildrum K., Isaksson T., Naes T. and Tandberg A. (eds.) Near Infra-red Spectroscopy. Bridging the gap between Data Analysis and NIR Applications. Horwood Chichester, UK: 41-446

In 1999, one plant of the F6 generation, 22044-3, had a GSL content of 17.3 μmol/g seed, while the seed of its sister plants had a GSL content between 22.5-23.8 μmol/g. Plant 22044-3 was selfed resulting in plants of the F7 generation. Seed of the 6797-2 plant had a GSL content of 11.4 μmol/g, while its sister plants had a GSL content from 24.6-25.7 μmol/g. The plant resulting from growing the seed of 6797-2 was selfed. In 2001 at F8, no single plant resulting from this selfing had seed with a GSL content above 14.3 μmol/g. The seed of plant 21615-7 had a GSL content of only 7.0 μmol/g. The average expression of seed from plants in plot 21615 was 10.7 μmol/g, which is at least 7 μmol lower than the lowest other reference restorer lines grown simultaneously in the same experimental field trial in Germany and more than 5 μmol below the standard plots of the non-restorer varieties Express and Laser. At the F9 generation, BLR-038 was produced by selfing of homozygous descendants of 21615-5.

TABLE 1

| Pollination | Year | Generation | PLOT | Cross | Plot μmol/g Seed | Single plant No. (GSL μmol/g seed at 9% H$_2$O) |
|---|---|---|---|---|---|---|
| cross | 1992 | | 92HR013 | R30195 (CMS B6 021) × R40 | | n.d.* |
| cross | 1993 | | 93HR141 | 92HR013 × 93B-1-3 | | n.d.* |
| cross | 1994 | F1 | 94HR233 | 93HR141 × 92/19047 | | n.d.* |
| selfing | 1995 | F2 | 21614 | | | 9 (n.d.*) |
| selfing | 1996 | F3 | 21969 | | | 3 (n.d.*) |

TABLE 1-continued

| Pollination | Year | Generation | PLOT | Cross | Plot µmol/g Seed | Single plant No. (GSL µmol/g seed at 9% H$_2$O) |
|---|---|---|---|---|---|---|
| selfing | 1997 | F4 | 22446 | | | 8 (n.d.*) |
| selfing | 1998 | F5 | 22590 | | | 1 (n.d.*) |
| selfing | 1999 | F6 | 22044 | GSL content of sister plants was 22.5-23.8 | | 3 (17.3) |
| selfing | 2000 | F7 | 6797 | GSL content of sister plants was 24.6-25.7 | | 2 (11.4) |
| selfing | 2001 | F8 | 21615 | No single plants with GSL content above 14.3 µmol were observed | 10.7 | 1 (10.3), 2 (9.4), 4 (14.1), 5 (8.6), 6 (9.4), 7 (7.0), 8 (14.3) |
| selfing | 2002 | F9 | | | | 3 (4.5); 6 (5.5); 7 (10.1); 8 (4.9); 10 (6.0); 11 (8.7).; 12 (4.2); 13 (5.2); 14 (12.5); 15 (6.4); 17 (3.6); 18 (7.7); |
| | | | 21615-5 | BLR-038 | | 19 (9.5)** |

*n.d. = not determined
**glass house data

Table 2 shows the segregation ratio for several of the single plants of plot 01-21615. The Rf pollinator plants (21615-01, 21615-05, 21615-06, 21615-08) are homozygous for the Rf gene (RfRf). F1 hybrids were produced from the cross of the homozygous Rf pollinator and CMS female lines. These crosses show a transmission of male fertility of approximately 100%.

TABLE 2

| | Homozygous Pollinator | | | | | | | |
|---|---|---|---|---|---|---|---|---|
| | F1 hybrids | | | | Selfing of Pollinator | | | |
| Pollinator Origin 2001 (F8) | plants | male sterile | male fertile | ratio fertile plants; expected 100% | plants | male sterile | male fertile | ratio fertile plants; expected 100% |
| 01 21615-01 | 12 | 0 | 12 | 100.0% | 9 | 0 | 9 | 100.0% |
| 01 21615-05 | 39 | 1 | 38 | 97.4% | 14 | 1 | 13 | 92.9% |
| 01 21615-06 | 16 | 0 | 16 | 100.0% | 12 | 0 | 12 | 100.0% |
| 01 21615-08 | 11 | 1 | 10 | 90.9% | 9 | 0 | 9 | 100.0% |
| SUM | 78 | 2 | 76 | 97.4% | 44 | 2 | 43 | 97.7% |

Example 2

Characterization of *Brassica* Inbred Line BLR-038 by Means of AFLP Analysis

A population consisting of 25 individuals segregating for the original Ogura restorer translocation was genotyped using a co-dominant PCR assay consisting of two proprietary SCAR markers derived from RAPD marker OPY17 that are in coupling or in repulsion phase to the restoration locus. Homozygous recessive (rf/rf) plants and restorer (RfRf and Rfrf) plants were bulked separately and used for the identification of AFLP markers putatively linked to the Rf gene. Such markers allowed for the comparison of BLR-038 to Pioneer hybrids 209002, 97839, 97838, 209001, and to SERASEM's hybrid Lutin containing the restorer locus released by Institut National de la Recherche Agronomique (INRA) in Rennes, France (Pelletier et al., 1987) Proc 7$^{th}$. Int. Rapeseed Conf., Poznan, Poland: 113-119. AFLP analysis was performed essentially as described by Vos et al. (1995) Nucleic Acids Research 23(21): 4407-4414.

First, 500 ng DNA for each sample BLR-038, 209002, 97839, 97838, 209001, and the hybrid Lutin, was digested in 40 µl of 1×TA-buffer (10 mM Tris-acetate, 10 mM MgAc, 50 mM KAc, 1 mM DTT, 2 µg BSA and 5 u each of EcoRI and TruI I (MBI Fermentas, Lithuania). EcoRI is in the following referred to as E, and TruI I, an isoschizomer of MseI, is referred to as M. The E and M adaptors are represented by the following sequences:

```
EcoRI-adaptor:  5'-CTCGTAGACTGCGTACC      SEQ ID NO: 21
                   CATCTGACGCATGGTTAA-5'  SEQ ID NO: 22
MseI-adaptor:   5'-GACGATGAGTCCTGAG       SEQ ID NO: 23
                   TACTCAGGACTCAT-5'      SEQ ID NO: 24
```

Following digestion, 10 µl of ligation solution containing 1×Ligation buffer (40 mM Tris-HCl (pH 7.8), 10 mM MgCl$_2$, 10 mM DTT, 0.5 mM ATP, 1 u T4 DNA ligase, 0.1 µM E-adapter and 1.0 µM M-adapter, sequences as described by Vos et al. (1995), was added directly to the DNA digest, incubated, and subsequently diluted 10-fold in 1×TE-buffer. To increase the amount of template DNA, the diluted ligation reactions were preamplified with primers having one additional and selective nucleotide each, i.e. E+1 and M+1, The primers used for the pre-amplification reaction consist of the same sequence as the adapters except for a one nucleotide extension at their 3' end. Primer E+A hybridizes to the EcoRI adapter and carries an additional A, the primer M+C hybridizes to the MseI adapter and carries an additional C. The reaction solution of 20 µl contained 5 µl of template DNA (10-fold diluted ligation reaction), 1×PCR-buffer II (10 mM Tris-HCl, pH 8.3), 50 mM KCl, 0.2 mM dNTP, 1.5 mM $MgCl_2$, 0.4 u Taq polymerase and 0.3 µM each of (E+A)-primer and (M+C)-primer. The pre-amplification reactions were performed in either Perkin-Elmer/Cetus 9600 or MJ Research PTC-100 thermocyclers using the following temperature profile: 20 cycles of 30 s at 94° C., 30 s at 56° C. and 60 s at 72° C.

Prior to selective amplification, (E+3)-primers were end-labelled in a solution containing 1×kinase buffer (50 mM Tris-HCl (pH 7.6), 10 nM $MgCl_2$, 5 mM DTT, 0.1 mM spermidine, 0.1 mM EDTA, 1.7 µM (L+3)-primer (DNA Technologies), 0.2 u/µl T4 polynucleotide kinase and 2 µCi/µl µ-$^{33}$P[ATP]. Selective amplification was performed using the following temperature profile: 12 cycles of 30 s at 94° C., 30 s at 65° C. ramping 0.7° C./cycle to 56° C., 60 s at 72° C., followed by 23 cycles of 30 s at 94° C., 30 s at 56° C., 60 s at 72° C. The reaction solution of 20 µl contained 5 µl pre-amplified template DNA, 0.5 µl labelled (E+3)-primer, 1×PCR-buffer II (Advanced Biotechnologies), 1.5 mM $MgCl_2$, 0.2 mM dNTP, 0.25 µM (M+3)-primer (DNA Technologies), and 0.4 u of Taq polymerase. After amplification 20 µl of formamide loading buffer (98% formamide, 10 mM EDTA, 0.1% each of xylene cyanol and bromophenol blue) was added and the samples were denatured at 95° C. for 3 min. Amplified fragments were separated on 5% polyacryamide gels consisting of 19:1 Acrylamide/Bis solution, 1×TBE-buffer, 0.10% TEMED and 0.03% APS. Custom-made gel apparatuses for 35 cm gels (CBS Scientific Co., USA) were used in all analyses. Gels were pre-run at 110 W for 30 min before loading of 3 µl sample and run at 110 W for 3 h. Following electrophoresis, gels were transferred to 3 MM-paper, dried on a gel dryer over night at 80° C., and exposed to film for 1-2 days.

All E+3 primers (24 nt in length) as shown in Table 3 (SEQ. ID No. 25 to 37) and the sequence listing carry an A at position 22 and all M+3 primers (21 nt in length) a C at position 19, which correspond to the extensions on the pre-amplification primers. The extensions at the pre-amplification primers are random and are added for the purpose of reducing the complexity of the template. Rather than amplifying the whole genome, only a fraction is amplified that subsequently is used as template in the final amplification using the E+3 and M+3 primers. The E+A and M+C pre-amplification primers are identical to the E+3 and M+3 primers respectively, but two nucleotides shorter. It is understood that one skilled in the art can develop additional primers by generating additional randomly generated extensions to the adaptors M and E. Some of these new primers would amplify additional nucleic acid segments or markers located along the nucleic acid segment derived from Ogura *Raphanus sativus* and would be categorized within one of the four bins. Those skilled in the art would recognize that these additional primers and markers fall within the scope of the claimed invention.

In total 48 primer combinations were screened, including the 7 primer pairs that were shown to deliver polymorphic bands in patent application WO98/56948. Only bands that were present in the Ogura Rf bulk but absent in the homozygous recessive bulk (rf/rf) were taken into consideration for the comparison of the *Brassica* inbred line BLR-038 to the hybrids released by Pioneer and MRA.

Table 3 shows all AFLP markers that revealed polymorphism between the bulk for the Ogura Rf translocation and the homozygous recessive (rf/rf) bulk. The markers are binned according to their amplification profile across the various plant materials. The results are represented in a schematic manner in Table 4, which reveals the four different classes of markers. Presence of a band is indicated with '1', its absence with '0'. A bin refers to a set of markers grouped according to their location along a nucleic acid segment. AFLP markers E5M16-1, E5M4-3, E6M3-2, and E8M14-1 are of bin 1, wherein these markers are amplified in all samples Lutin, P209001, P97838, P97839, BLR-038, and P209002. ALFP markers E2M4-1, E3M1-1, E4M14-1, E5M1-2, E5M4-2, E8M14-2 are of bin 2, wherein bin 2 markers amplify Lutin, P209001, P97838, P97839, BLR-038, but not P209002. The AFLP marker E8M1-2 is of bin 3, wherein bin 3 markers amplify Lutin, P209001, P97838, P97839, but not BLR-038, and P209002. The AFLP markers E2M13-1, E2M14-1, E3M12-1, and E6M3-1 are of bin 4, wherein bin 4 markers amplify Lutin and P209001, but not P97838, P97839, BLR-038, and P209002.

Example 3

Characterization of the *Brassica* Inbred Line BLR-038 Using SCAR Markers

Primer pairs were designed to the nucleotide sequences of the amplification products for the RAPD, AFLP and SCAR markers in coupling phase with the Ogura restorer gene as disclosed in patent application CA2,206,673: OPC2 (Seq ID No. 2 and 7), OPN20 (Seq ID No. 3 and 8), OPF10 (Seq ID No. 4 and 10), OPH3 (Seq ID No. 9), OPH15 (Seq ID No. 11), E36xM48AIII ((Seq ID No. 12), E35xM62AV (Seq ID No. 13), E33xM47A1 (Seq ID No. 14), and E38xM60A1 (Seq ID No. 15). In addition to these markers, primers were designed to the nucleotide sequence of RAPD marker OPH11 that was shown to be associated to fertility restoration in Raphanus where the Ogura locus originates (Accession number ABO51636). The sequences of all primers assayed as well as the size of the expected amplification products are listed in Table 3. The primer combinations including the proprietary SCAR marker derived from RAPD marker OPY17, were used to analyze the original Ogura translocation, BLR038, Pioneer hybrids 209002, 97839, 97838, 209001, and the hybrid Lutin using a standard PCR protocol. After PCR, the amplification products were visualized by means of agarose gel electrophoresis. Referring to Table 4, the SCAR markers OPF10, OPC2 AND E35M62 are markers of Bin 1. Markers that fall within Bin 1, as discussed above, are characterized as amplifying the samples Lutin, P209001, P97838, P97839, BLR-038, and P209002. The SCAR marker E33M47 is of bin 2. Bin 2 markers are characterized as amplifying the samples Lutin, P209001, P97838, P97839, BLR-038, but not P209002. The two SCAR markers, OPY17 and OPN20 of Bin 3, are characterized by amplifying the samples Lutin, P209001, P97838, P97839, but not BLR-038, and P209002. Bin 4 SCAR markers, such as OPH15 and E36M48, amplify Lutin and P209001, but not P97838, P97839, BLR-038, and P209002.

TABLE 3

| Marker Locus | Primer Pair | | Sequence | Product Size | Origin of sequence |
|---|---|---|---|---|---|
| SCAR markers and primers | | | | | |
| OPC2 | 1127 | (SEQ ID NO: 1) | ggggaaggaaggaaggactc | 677 bp | CA 2,206,673 |
| | 1128 | (SEQ ID NO: 2) | tcaggttcacacagcagcata | | |
| OPN20 | 1135 | (SEQ ID NO: 3) | ataggttcctggcagagatg | 630 bp | CA 2,206,673 |
| | 1136 | (SEQ ID NO: 4) | atagcagtcagaaaccgctc | | |
| OPF10 | 1137 | (SEQ ID NO: 5) | ctgatgaatctcggtgagac | 760 bp | CA 2,206,673 |
| | 1138 | (SEQ ID NO: 6) | ccgtatgccttggttatctc | | |
| OPH15 | 1218 | (SEQ ID NO: 7) | tctgtaaatcctttccaccc | 601 bp | CA 2,206,673 |
| | 1219 | (SEQ ID NO: 8) | aaaaaagcacccgagaatct | | |
| E36M48 | 1222 | (SEQ ID NO: 9) | gcgtgatgatctgttgagaa | 251 bp | CA 2,206,673 |
| | 1223 | (SEQ ID NO: 10) | ggatttgtgggattggaaa | | |
| E35M62 | 1224 | (SEQ ID NO: 11) | gaggttcaggaatgctgttt | 201 bp | CA 2,206,673 |
| | 1225 | (SEQ ID NO: 12) | gctcctgttagtgactcttca | | |
| E33M47 | 1159 | (SEQ ID NO: 13) | taacaaaatagagggagaggatg | 140 bp | CA 2,206,673 |
| | 1160 | (SEQ ID NO: 14) | caagattatagctacctaacagg | | |
| Gene 16 | 16-1 | (SEQ ID NO: 15) | tgttcagcatttagtttcgccc | 471 bp | WO 03/006622 |
| | 16-2 | (SEQ ID NO: 16) | ttgttcagttccaccaccagcc | | |
| Gene 26 | 26-1 | (SEQ ID NO: 17) | gctcacctcatccatcttcctcag | 530 bp | WO 03/006622 |
| | 26-2 | (SEQ ID NO: 18) | ctcgtcctttaccttctgtggttg | | |
| OPY17 | PR0004F | (SEQ ID NO: 19) | acgtggtgaggacatgccctttctg | 300 bp | Syngenta |
| | PR0004R | (SEQ ID NO: 20) | ctggtgtattctacctcatcattaaa | | |
| | PR0001F1 | (SEQ ID NO: 40) | gacgtggtgaacaagatg | | |
| | PR0001R1 | (SEQ ID NO 41) | acgtggtgataataaattggc | 420 bp | Syngenta |
| AFLP markers and primers | | | | | |
| E2M4 | E2 | (SEQ ID NO: 25) | ctcgtagactgcgtaccaattaac | | |
| | M4 | (SEQ ID NO: 26) | gacgatgagtcctgagtacat | | |
| E2M13 | E2 | | | | |
| | M13 | (SEQ ID NO: 27) | gacgatgagtcctgagtacta | | |
| E2M14 | E2 | | | | |
| | M14 | (SEQ ID NO: 28) | gacgatgagtcctgagtactc | | |
| E3M1 | E3 | (SEQ ID NO: 29) | ctcgtagactgcgtaccaattaag | | |
| | M1 | (SEQ ID NO: 30) | gacgatgagtcctgagtacaa | | |
| E3M12 | E3 | | | | |
| | M12 | (SEQ ID NO: 31) | gacgatgagtcctgagtacgt | | |
| E4M14 | E4 | (SEQ ID NO: 32) | ctcgtagactgcgtaccaattaat | | |
| | M14 | | | | |
| E5M1 | E5 | (SEQ ID NO: 33) | ctcgtagactgcgtaccaattaca | | |
| | M1 | | | | |
| E5M4 | E5 | | | | |
| | M4 | | | | |
| E5M16 | E5 | | | | |
| | M16 | (SEQ ID NO: 34) | gacgatgagtcctgagtactt | | |
| E6M3 | E6 | (SEQ ID NO: 35) | ctcgtagactgcgtaccaattacc | | |
| | M3 | (SEQ ID NO: 36) | gacgatgagtcctgagtacag | | |
| E8M1 | E8 | (SEQ ID NO: 37) | ctcgtagactgcgtaccaattact | | |
| | M1 | | | | |
| E8M14 | E8 | | | | |
| | M14 | | | | |

TABLE 4

| Marker | Type | Rfrf 1 | rfrf 2 | Lutin 8 | P 209001 6 | P 97838 4 | P 97839 5 | BLR-038 3 | P 209002 7 | |
|---|---|---|---|---|---|---|---|---|---|---|
| OPF10 | SCAR | + | 0 | + | + | + | + | + | + | |
| OPC2 | SCAR | + | 0 | + | + | + | + | + | + | |
| E35M62 | SCAR | + | 0 | + | + | + | + | + | + | |
| E5M16-1 | AFLP | + | 0 | + | + | + | + | + | + | BIN 1 |
| E5M4-3 | AFLP | + | 0 | + | + | + | + | + | + | |
| E6M3-2 | AFLP | + | 0 | + | + | + | + | + | + | |
| E8M14-1 | AFLP | + | 0 | + | + | + | + | + | + | |
| E33M47 | SCAR | + | 0 | + | + | + | + | + | 0 | |
| E2M4-1 | AFLP | + | 0 | + | + | + | + | + | 0 | |
| E3M1-1 | AFLP | + | 0 | + | + | + | + | + | 0 | |
| E4M14-1 | AFLP | + | 0 | + | + | + | + | + | 0 | BIN 2 |
| E5M1-2 | AFLP | + | 0 | + | + | + | + | + | 0 | |
| E5M4-2 | AFLP | + | 0 | + | + | + | + | + | 0 | |
| E8M14-2 | AFLP | + | 0 | + | + | + | + | + | 0 | |
| OPY17 | SCAR | + | 0 | + | + | + | + | 0 | 0 | |
| OPN20 | SCAR | + | 0 | + | + | + | + | 0 | 0 | BIN 3 |
| E8M1-2 | AFLP | + | 0 | + | + | + | + | 0 | 0 | |
| OPH15 | SCAR | + | 0 | + | + | 0 | 0 | 0 | 0 | |
| E36M48 | SCAR | + | 0 | + | + | 0 | 0 | 0 | 0 | |
| E2M13-1 | AFLP | + | 0 | + | + | 0 | 0 | 0 | 0 | |
| E2M14-1 | AFLP | + | 0 | + | + | 0 | 0 | 0 | 0 | BIN 4 |
| E3M12-1 | AFLP | + | 0 | + | + | 0 | 0 | 0 | 0 | |
| E6M3-1 | AFLP | + | 0 | + | + | 0 | 0 | 0 | 0 | |

Example 4

Kit and Method for Detecting the BLR1 Recombination Event

Total DNA is isolated from approximately 1 cm² of *Brassica* leaf tissue by using the Wizard® Magnetic 96 DNA Plant System (Promega). In one embodiment, the Multiplex PCR kit and method of the present invention detects the presence or absence of PCR amplification products corresponding to OPY17 (Bin 3) and E33M47 (Bin 2).

The four primers PR0004F, PR0004R, 1159 and 1160 (Table 4) are added to a reaction mixture at a concentration of 7.5 µmol each. Except for the multiplex nature, the composition of the PCR reaction is standard in the art, using Platinum Taq polymerase from Invitrogen. Amplification conditions are as follows: 5 minutes of initial denaturation at 94° C. were followed by 35 cycles of 30 seconds at 94° C., 30 seconds at 57° C., and 90 seconds at 72° C. PCR amplification products were separated on 2.0% agarose gels.

As a results of the PCR reaction, the presence of the BLR1 recombination event is established when the primers amplify the 140 bp product that corresponds to E33M47, but does not amplify the 300 bp product that corresponds to OPY17. It was also shown that the PCR reaction amplified both OPY17 and E33M47 for the original Ogura restorer translocation fragment as well as the derived recombination events Pioneer 97838, 97839, 209001, and the Lutin event from INRA. Pioneer recombination event 209002 on the other hand, shows neither the E33M47, nor the OPY17 amplification product. These results demonstrate that primers that selectively amplify markers from Bin 2 and 3, such as E33M47 and OPY17, are successfully used in a single multiplex PCR assay to distinguish and identify the BLR1 recombination event in plant material.

It is understood that the kit and method of the present invention incorporate one or more of markers falling within Bin 3 and one or more markers falling within Bin 2 to detect the presence of the BLR1 recombination event in plants. It is within the scope of the claimed invention to develop and use additional markers that fall within one of the bins 1, 2, 3, or 4 in accordance with the methods described herein.

Example 5

Improvement of Restorer

The *Brassica* inbred line BLR-038, Deposit Number NCIMB 41193 deposited on Aug. 28, 2003, was crossed with high performing winter oilseed rape breeding lines, which are used as recurrent parents. In these crosses, the inbred line BLR-038 was used as female to maintain the CMS cytoplasm. In thus obtained F1 plants were crossed with the recurrent parents to replace more of the genome of the inbred line BLR-038. Due to the CMS cytoplasm in every generation the presence or absence of the restorer gene could be detected by fertility scoring. In the F2 generation homozygous restorer plants were detected in the greenhouse by the described marker analysis and selfed. F3 descendants of the homozygous F2 plants were planted into the field to select only within the desired homozygous restorer plants. This helped to overcome a reduced amount of homozygous offsprings that were shown by the testcrosses. F3 plants are then selfed. Testcrosses were performed by using several CMS Ogura male sterile lines with a set of genetically different F4 or subsequent generation inbred plants as the female parents containing the BLR1 recombination event of the invention. The descendants were sown in the greenhouse and fertile and sterile plants were counted during flowering. Plants containing BLR1 recombination event can also be selected using the kit and method described herein.

Example 6

Hybrid Development

A conventional hybrid production scheme is applied using CMS Ogura and restorer line. As explained above, a male-sterile, female CMS A-line cannot self-pollinate, so it is maintained by crossing it with a maintainer B-line that is male fertile and genetically identical to the A-Line. The result of this cross is a male-sterile CMS A-line. The restorer R-line can be maintained by selfing.

The restorer R-line is crossed with the male sterile CMS line to produce F1 seed produced on the A-line.

The F1 seed are sold commercially for the production of F2 seed. The F2 seed of the invention has a low glucosinolate level as shown in Table 5. Table 5 shows the use of the Brassica inbred line BLR-038 to pollinate three different CMS inbred lines to produce three different hybrids. The GSL content of the F2 seed produced by the fertilized CMS plants showed substantially lower GSL content than a conventional Ogura restorer hybrid and are comparable to the desirable GSL levels of conventional non-restorer lines such as EXPRESS and SMART.

Example 7

Creating Hybrids from a Cross cms Line x BLR01 Line

A cross was made between line BLR-038, Deposit Number NCIMB 41193 deposited on Aug. 28, 2003 and the proprietary breeding line 01 25853-03. Plants of the F1 Generation were selfed in the greenhouse. The F2 Generation was sown into the field and in spring of the following year the plants of the F2 generation were analyzed with two markers using a co-dominant PCR assay consisting of two SCAR markers that are in coupling or in repulsion phase to the restoration locus. Some of the identified homozygous restorer plants were transplanted into a seed multiplication isolation alongside with the male sterile line RNX 4801. The plot with the two parents was isolated by a net to avoid cross pollination. From the male sterile female parent 760 g hybrid seed were harvested and sown into a 7 location yield trial to determine the yield, agronomy and quality parameters of fully restored BLR hybrids.

Example 8

Determination of Ogura Rf-Genotype

One possibility to determine whether a plant, for example a F2 plant coming from a cross between a Ogura-cms line and a Ogura-restorer line, is a homozygous restorer, a homozygous maintainer or a heterozygous restorer, is to test this plant with a molecular marker for the restorer locus and with a molecular marker for the non-restorer locus. For this test the four primers PR0001F1 (SEQ ID NO 40), PR0001R1 (SEQ ID NO 41), 1137 (SEQ ID NO: 5) and 1138 (SEQ ID NO: 6) are added to a reaction mixture at a concentration of 7.5 pmol each. Except for the multiplex nature, the composition of the PCR reaction is standard in the art, using Platinum Taq polymerase from Invitrogen. Amplification conditions are as follows: 5 minutes of initial denaturation at 94° C. were followed by 35 cycles of 30 seconds at 94° C., 30 seconds at ° C., and 90 seconds at 72° C. PCR amplification products are separated on a 2.0% agarose gel.

If there is only one PCR product around 760 bp the plant is a homozygous restorer plant. If there is only a PCR product around 420 bp, the plant is a maintainer. And if there are both of the PCR products (420 bp and 760 bp) the plant is a heterozygous restorer plant.

Alternatively a dot-blot detection assay can be used according to what is described in CA 2,206,673.

TABLE 5

| | Oil % | GSL μmol |
|---|---|---|
| CMS female parent × BLR-038 | | |
| CMS line RNX 4801 × 01 21615-05 (BLR 038 Restorer) | 40 | 13.9 |
| CMS line RNX 4002 × 01 21615-08 (BLR 038 Restorer) | 38 | 16.65 |
| CMS line RNX 4901 × 01 21615-05(BLR 038 Restorer) | 41.9 | 12.55 |
| CMS line RNX 4801 × RNX 6001 (conventional Restorer) | 41.3 | 29.7 |
| EXPRESS (conventional line variety) | 39.3 | 15.6 |
| SMART (conventional line variety) | 39.9 | 12.0 |

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. A method of detecting a *Brassica* plant containing a restorer gene, comprising the steps of:
   a) obtaining a sample from a *Brassica* plant;
   b) detecting in said sample a DNA fragment by
      ii) at least one marker of bin 2, but none of the markers of bin 3; or
      iii) all the markers of bin 2, but none of the markers of bin 3, wherein bin 2 is defined as consisting of the markers E33M47, E2M4-1, E3M1-1, E4M141, E5M1-2, E5M4-2, and E8M14-2 and bin 3 is defined as consisting of OPY17, OPN20, and E8M1-2.

2. The method of detecting a *Brassica* plant according to claim 1, further comprising selecting said *Brassica* plant, or a part thereof, containing said DNA fragment.

3. The method of detecting a *Brassica* plant according to claim 1, further comprising the step of selfing said *Brassica* plant containing said DNA fragment.

4. The method of detecting a *Brassica* plant according to claim 1, further comprising the step of crossing said *Brassica* plant with another *Brassica* plant.

5. The method of detecting a *Brassica* plant according to claim 1, wherein said DNA fragment comprises the BLR1 recombination event.

6. The method of detecting a *Brassica* plant according to claim 1, further comprising the step of detecting in said sample a DNA fragment obtainable by PCR amplification using primers SEQ ID NO: 13 (1159) and SEQ ID NO: 14 (1160), whereas said DNA fragment is not amplified by the primers SEQ ID NO: 19 (PR0004F) and SEQ ID NO: 20 (PR0004R).

7. A method for producing a fertile F1 hybrid *Brassica* plant comprising the steps of:
   a) detecting in seed or a plant of the male fertile restorer parent the BLR1 recombination event characterized by having
      i) at least one marker of bin 2, but none of the markers of bin 3; or
      ii) all the markers of bin 2, but none of the markers of bin 3, wherein bin 2 is defined as consisting of the markers E33M47, E2M4-1, E3M1-1, E4M141, E5M1-2, E5M4-2, and E8M14-2 and bin 3 is defined as consisting of OPY17, OPN20, and E8M1-2; and
   b) crossing the female and male parents to produce F1 hybrid seed.

8. The method for producing a fertile F1 hybrid *Brassica* plant according to claim 7, comprising the additional step of planting said F1 hybrid seed.

9. The method for producing a fertile F1 hybrid *Brassica* plant according to claim 8, comprising the additional step of harvesting the F2 seed grown from the plant resulting from said F1 seed.

10. A method according to claim 9 comprising the additional step of determining total glucosinolate content in F2 seed derived from the F1 hybrid plant.

11. A hybrid F1 *Brassica* plant produced by the method of claim 8.

12. A method for producing a *Brassica* plant containing the BLR1 recombination event comprising the steps of obtaining a *Brassica* plant containing the BLR1 recombination event characterized by having at least one marker of bin 2, but none of the markers of bin 3; or all the markers of bin 2, but none of the markers of bin 3, wherein bin 2 is defined as consisting of the markers E33M47, E2M4-1, E3M1-1, E4M141, E5M1-2, E5M4-2, and E8M14-2 and bin 3 is defined as consisting of OPY17, OPN20, and E8M1-2, crossing this plant containing the BLR1 recombination event with a another *Brassica* plant, obtaining hybrid seed produced by this cross, and planting said hybrid seed to produce a *Brassica* plant containing the BLR1 recombination event.

* * * * *

SEQUENCE LISTING

```
<160> NUMBER OF SEQ ID NOS: 41

<210> SEQ ID NO 1
<211> LENGTH: 20
<212> TYPE: DNA
<213> ORGANISM: Artificial Sequence
<220> FEATURE:
<223> OTHER INFORMATION: Artificially synthesized Primer 1127

<400> SEQUENCE: 1
ggggaaggaa ggaaggactc                                              20

<210> SEQ ID NO 2
<211> LENGTH: 21
<212> TYPE: DNA
<213> ORGANISM: Artificial Sequence
<220> FEATURE:
<223> OTHER INFORMATION: Artificially synthesized Primer 1128

<400> SEQUENCE: 2
tcaggttcac acagcagcat a                                            21
```

```
<210> SEQ ID NO 3
<211> LENGTH: 20
<212> TYPE: DNA
<213> ORGANISM: Artificial Sequence
<220> FEATURE:
<223> OTHER INFORMATION: Artificially synthesized Primer 1135

<400> SEQUENCE: 3
ataggttcct ggcagagatg                                           20

<210> SEQ ID NO 4
<211> LENGTH: 20
<212> TYPE: DNA
<213> ORGANISM: Artificial Sequence
<220> FEATURE:
<223> OTHER INFORMATION: Artificially synthesized Primer 1136

<400> SEQUENCE: 4
atagcagtca gaaaccgctc                                           20

<210> SEQ ID NO 5
<211> LENGTH: 20
<212> TYPE: DNA
<213> ORGANISM: Artificial Sequence
<220> FEATURE:
<223> OTHER INFORMATION: Artificially synthesized Primer 1137

<400> SEQUENCE: 5
ctgatgaatc tcggtgagac                                           20

<210> SEQ ID NO 6
<211> LENGTH: 20
<212> TYPE: DNA
<213> ORGANISM: Artificial Sequence
<220> FEATURE:
<223> OTHER INFORMATION: Artificially synthesized Primer 1138

<400> SEQUENCE: 6
ccgtatgcct tggttatctc                                           20

<210> SEQ ID NO 7
<211> LENGTH: 20
<212> TYPE: DNA
<213> ORGANISM: Artificial Sequence
<220> FEATURE:
<223> OTHER INFORMATION: Artificially synthesized Primer 1218

<400> SEQUENCE: 7
tctgtaaatc ctttccaccc                                           20

<210> SEQ ID NO 8
<211> LENGTH: 20
<212> TYPE: DNA
<213> ORGANISM: Artificial Sequence
<220> FEATURE:
<223> OTHER INFORMATION: Artificially synthesized Primer 1219

<400> SEQUENCE: 8
aaaaaagcac ccgagaatct                                           20

<210> SEQ ID NO 9
<211> LENGTH: 20
<212> TYPE: DNA
<213> ORGANISM: Artificial Sequence
<220> FEATURE:
<223> OTHER INFORMATION: Artificially synthesized Primer 1222
```

<400> SEQUENCE: 9
gcgtgatgat ctgttgagaa                                              20

<210> SEQ ID NO 10
<211> LENGTH: 19
<212> TYPE: DNA
<213> ORGANISM: Artificial Sequence
<220> FEATURE:
<223> OTHER INFORMATION: Artificially synthesized Primer 1223

<400> SEQUENCE: 10
ggatttgtgg gattggaaa                                               19

<210> SEQ ID NO 11
<211> LENGTH: 20
<212> TYPE: DNA
<213> ORGANISM: Artificial Sequence
<220> FEATURE:
<223> OTHER INFORMATION: Artificially synthesized Primer 1224

<400> SEQUENCE: 11
gaggttcagg aatgctgttt                                              20

<210> SEQ ID NO 12
<211> LENGTH: 21
<212> TYPE: DNA
<213> ORGANISM: Artificial Sequence
<220> FEATURE:
<223> OTHER INFORMATION: Artificially synthesized Primer 1225

<400> SEQUENCE: 12
gctcctgtta gtgactcttc a                                            21

<210> SEQ ID NO 13
<211> LENGTH: 23
<212> TYPE: DNA
<213> ORGANISM: Artificial Sequence
<220> FEATURE:
<223> OTHER INFORMATION: Artificially synthesized Primer 1159

<400> SEQUENCE: 13
taacaaaata gagggagagg atg                                          23

<210> SEQ ID NO 14
<211> LENGTH: 23
<212> TYPE: DNA
<213> ORGANISM: Artificial Sequence
<220> FEATURE:
<223> OTHER INFORMATION: Artificially synthesized Primer 1160

<400> SEQUENCE: 14
caagattata gctacctaac agg                                          23

<210> SEQ ID NO 15
<211> LENGTH: 22
<212> TYPE: DNA
<213> ORGANISM: Artificial Sequence
<220> FEATURE:
<223> OTHER INFORMATION: Artificially synthesized Primer 16-1

<400> SEQUENCE: 15
tgttcagcat ttagtttcgc cc                                           22

<210> SEQ ID NO 16
<211> LENGTH: 22

-continued

```
<212> TYPE: DNA
<213> ORGANISM: Artificial Sequence
<220> FEATURE:
<223> OTHER INFORMATION: Artificially synthesized Primer 16-2

<400> SEQUENCE: 16
ttgttcagtt ccaccaccag cc                                           22

<210> SEQ ID NO 17
<211> LENGTH: 24
<212> TYPE: DNA
<213> ORGANISM: Artificial Sequence
<220> FEATURE:
<223> OTHER INFORMATION: Artificially synthesized Primer 26-1

<400> SEQUENCE: 17
gctcacctca tccatcttcc tcag                                         24

<210> SEQ ID NO 18
<211> LENGTH: 24
<212> TYPE: DNA
<213> ORGANISM: Artificial Sequence
<220> FEATURE:
<223> OTHER INFORMATION: Artificially synthesized Primer 26-2

<400> SEQUENCE: 18
ctcgtccttt accttctgtg gttg                                         24

<210> SEQ ID NO 19
<211> LENGTH: 25
<212> TYPE: DNA
<213> ORGANISM: Artificial Sequence
<220> FEATURE:
<223> OTHER INFORMATION: Artificially synthesized Primer PR0004F

<400> SEQUENCE: 19
acgtggtgag gacatgccct ttctg                                        25

<210> SEQ ID NO 20
<211> LENGTH: 26
<212> TYPE: DNA
<213> ORGANISM: Artificial Sequence
<220> FEATURE:
<223> OTHER INFORMATION: Artificially synthesized Primer PR0004R

<400> SEQUENCE: 20
ctggtgtatt ctacctcatc attaaa                                       26

<210> SEQ ID NO 21
<211> LENGTH: 17
<212> TYPE: DNA
<213> ORGANISM: Artificial Sequence
<220> FEATURE:
<223> OTHER INFORMATION: Artificially synthesized EcoRI-adapter Forward
      primer

<400> SEQUENCE: 21
ctcgtagact gcgtacc                                                 17

<210> SEQ ID NO 22
<211> LENGTH: 18
<212> TYPE: DNA
<213> ORGANISM: Artificial Sequence
<220> FEATURE:
<223> OTHER INFORMATION: Artificially synthesized EcoRI-adapter Reverse
      primer

<400> SEQUENCE: 22
```

```
aattggtacg cagtctac                                                  18

<210> SEQ ID NO 23
<211> LENGTH: 16
<212> TYPE: DNA
<213> ORGANISM: Artificial Sequence
<220> FEATURE:
<223> OTHER INFORMATION: Artificially synthesized MseI-adapter Forward
      primer

<400> SEQUENCE: 23
gacgatgagt cctgag                                                    16

<210> SEQ ID NO 24
<211> LENGTH: 14
<212> TYPE: DNA
<213> ORGANISM: Artificial Sequence
<220> FEATURE:
<223> OTHER INFORMATION: Artificially synthesized MseI-adapter Reverse
      primer

<400> SEQUENCE: 24
tactcaggac tcat                                                      14

<210> SEQ ID NO 25
<211> LENGTH: 24
<212> TYPE: DNA
<213> ORGANISM: Artificial Sequence
<220> FEATURE:
<223> OTHER INFORMATION: Artificially synthesized primer E2

<400> SEQUENCE: 25
ctcgtagact gcgtaccaat taac                                           24

<210> SEQ ID NO 26
<211> LENGTH: 21
<212> TYPE: DNA
<213> ORGANISM: Artificial Sequence
<220> FEATURE:
<223> OTHER INFORMATION: Artificially synthesized Primer M4

<400> SEQUENCE: 26
gacgatgagt cctgagtaca t                                              21

<210> SEQ ID NO 27
<211> LENGTH: 21
<212> TYPE: DNA
<213> ORGANISM: Artificial Sequence
<220> FEATURE:
<223> OTHER INFORMATION: Artificially synthesized Primer M13

<400> SEQUENCE: 27
gacgatgagt cctgagtact a                                              21

<210> SEQ ID NO 28
<211> LENGTH: 21
<212> TYPE: DNA
<213> ORGANISM: Artificial Sequence
<220> FEATURE:
<223> OTHER INFORMATION: Artificially synthesized Primer M14

<400> SEQUENCE: 28
gacgatgagt cctgagtact c                                              21

<210> SEQ ID NO 29
<211> LENGTH: 24
```

```
<212> TYPE: DNA
<213> ORGANISM: Artificial Sequence
<220> FEATURE:
<223> OTHER INFORMATION: Artificially synthesized Primer E3

<400> SEQUENCE: 29
ctcgtagact gcgtaccaat taag                                        24

<210> SEQ ID NO 30
<211> LENGTH: 21
<212> TYPE: DNA
<213> ORGANISM: Artificial Sequence
<220> FEATURE:
<223> OTHER INFORMATION: Artificially synthesized Primer M1

<400> SEQUENCE: 30
gacgatgagt cctgagtaca a                                           21

<210> SEQ ID NO 31
<211> LENGTH: 21
<212> TYPE: DNA
<213> ORGANISM: Artificial Sequence
<220> FEATURE:
<223> OTHER INFORMATION: Artificially synthesized Primer M12

<400> SEQUENCE: 31
gacgatgagt cctgagtacg t                                           21

<210> SEQ ID NO 32
<211> LENGTH: 24
<212> TYPE: DNA
<213> ORGANISM: Artificial Sequence
<220> FEATURE:
<223> OTHER INFORMATION: Artificially synthesized Primer E4

<400> SEQUENCE: 32
ctcgtagact gcgtaccaat taat                                        24

<210> SEQ ID NO 33
<211> LENGTH: 24
<212> TYPE: DNA
<213> ORGANISM: Artificial Sequence
<220> FEATURE:
<223> OTHER INFORMATION: Artificially synthesized Primer E5

<400> SEQUENCE: 33
ctcgtagact gcgtaccaat taca                                        24

<210> SEQ ID NO 34
<211> LENGTH: 21
<212> TYPE: DNA
<213> ORGANISM: Artificial Sequence
<220> FEATURE:
<223> OTHER INFORMATION: Artificially synthesized Primer M16

<400> SEQUENCE: 34
gacgatgagt cctgagtact t                                           21

<210> SEQ ID NO 35
<211> LENGTH: 24
<212> TYPE: DNA
<213> ORGANISM: Artificial Sequence
<220> FEATURE:
<223> OTHER INFORMATION: Artificially synthesized Primer E6

<400> SEQUENCE: 35
ctcgtagact gcgtaccaat tacc                                        24
```

<210> SEQ ID NO 36
<211> LENGTH: 21
<212> TYPE: DNA
<213> ORGANISM: Artificial Sequence
<220> FEATURE:
<223> OTHER INFORMATION: Artificially synthesized Primer M3

<400> SEQUENCE: 36
gacgatgagt cctgagtaca g                                         21

<210> SEQ ID NO 37
<211> LENGTH: 24
<212> TYPE: DNA
<213> ORGANISM: Artificial Sequence
<220> FEATURE:
<223> OTHER INFORMATION: Artificially synthesized Primer E8

<400> SEQUENCE: 37
ctcgtagact gcgtaccaat tact                                      24

<210> SEQ ID NO 38
<211> LENGTH: 626
<212> TYPE: DNA
<213> ORGANISM: Artificial Sequence
<220> FEATURE:
<223> OTHER INFORMATION: Artificially synthesized Marker sequence

<400> SEQUENCE: 38
gacgtggtga taaaagcgga gaagatggca tccctatgct actgaagatt ccacgcatgt     60
tcgatccgtg gggaggctac agcattattg gattcggtga tattcttttg cccggtttgc    120
taatcgcatt tgctctcagg tccaaaaacc tttttttatc atctcagagt ttcctttcac    180
cgagttccaa gttttcctaa catttgtttc ttctttgcag atatgactgg ttagctaaca    240
agactcttcg aaccggctat tttatatggg cgatggttgc ttacggatta ggtaaaaaaa    300
tcacacacaa atccgcataa tctcactggt gtattctacc tcatcattaa aaccatttga    360
aaacctcgca ggtctttga ttacttacgt ggctctaaac ctaatggatg gacacggcca    420
accagcattg ctctacattg tccctttac tctcggttag ctggaaaatc tctctctctt    480
attcctctct ataacggcat tgaatgagta ttgagagaaa tctcgtgatg aaaaatatag    540
gaacgatgct tacactagct cgaaaacgag acgacctttg gactctatgg acgaaagagc    600
cagaaagggc atgtcctcac cacgtc                                   626

<210> SEQ ID NO 39
<211> LENGTH: 10
<212> TYPE: DNA
<213> ORGANISM: Artificial Sequence
<220> FEATURE:
<223> OTHER INFORMATION: Artificially synthesized RAPD primer Y17

<400> SEQUENCE: 39
gacgtggtga                                                      10

<210> SEQ ID NO 40
<211> LENGTH: 18
<212> TYPE: DNA
<213> ORGANISM: Artificial Sequence
<220> FEATURE:
<223> OTHER INFORMATION: Artificially synthesized Primer PR0001F1

<400> SEQUENCE: 40
gacgtggtga acaagatg                                             18

```
<210> SEQ ID NO 41
<211> LENGTH: 21
<212> TYPE: DNA
<213> ORGANISM: Artificial Sequence
<220> FEATURE:
<223> OTHER INFORMATION: Artificially synthesized Primer PR0001R1

<400> SEQUENCE: 41
acgtggtgat aataaattgg c                                              21
```